(12) United States Patent
Siccardi et al.

(10) Patent No.: US 12,285,179 B2
(45) Date of Patent: Apr. 29, 2025

(54) SURGICAL DEVICE

(71) Applicant: MEDACTA INTERNATIONAL SA, Castel San Pietro (CH)

(72) Inventors: Francesco Siccardi, Castel San Pietro (CH); Sascha Berberich, Castel San Pietro (CH); Gianluca Parisi, Castel San Pietro (CH); Riccardo Lucchini, Castel San Pietro (CH); Luka Cakic, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 730 days.

(21) Appl. No.: 17/598,084

(22) PCT Filed: Mar. 11, 2020

(86) PCT No.: PCT/IB2020/052090
§ 371 (c)(1),
(2) Date: Sep. 24, 2021

(87) PCT Pub. No.: WO2020/201855
PCT Pub. Date: Oct. 8, 2020

(65) Prior Publication Data
US 2022/0183704 A1 Jun. 16, 2022

(30) Foreign Application Priority Data
Mar. 29, 2019 (IT) .......................... 102019000004739

(51) Int. Cl.
*A61B 17/17* (2006.01)

(52) U.S. Cl.
CPC .................. *A61B 17/1764* (2013.01)

(58) Field of Classification Search
CPC .................. A61B 17/1714; A61B 17/1764
See application file for complete search history.

(56) References Cited

U.S. PATENT DOCUMENTS 5,458,602 A * 10/1995 Goble ................ A61B 17/1714
606/98
5,755,721 A * 5/1998 Hearn ................ A61B 17/1728
606/86 R (Continued)

OTHER PUBLICATIONS

International Search Report and Written Opinion issued in PCT/IB2020/052090, mailed May 12, 2020, 14 pages.

Primary Examiner — Matthew J Lawson
(74) Attorney, Agent, or Firm — Meunier Carlin & Curfman LLC (57) ABSTRACT

A surgical device comprising a handling member comprising a sleeve with a central slot and a guiding pin, a guiding element that can be slid into the central slot and externally having a guiding groove that is slidably coupled to a guiding pin, locking means configured to lock the sliding of the guiding element inside the central slot, and switchable between an activation configuration, wherein the movement of the guiding element inside said central slot is prevented, and a deactivation configuration, wherein the movement of the guiding element is free. The guiding groove comprises a first and a second rectilinear groove portion, angularly spaced apart and mutually interconnected by means of a transversal connecting groove portion interposed between said first and said second rectilinear groove portions.

9 Claims, 5 Drawing Sheets

(56) References Cited

U.S. PATENT DOCUMENTS

| | | | | |
|---|---|---|---|---|
| 6,210,415 B1* | 4/2001 | Bester | ............... | A61B 17/1714 |
| | | | | 606/96 |
| 8,287,547 B2 | 10/2012 | Martin et al. | | |
| 8,425,573 B2* | 4/2013 | Erickson | ............ | A61B 17/1728 |
| | | | | 606/104 |
| 2004/0106928 A1* | 6/2004 | Ek | ...................... | A61B 17/1675 |
| | | | | 623/20.14 |
| 2006/0195112 A1* | 8/2006 | Ek | ...................... | A61B 17/1617 |
| | | | | 606/86 R |
| 2012/0071876 A1* | 3/2012 | Stoll | ................. | A61B 17/1631 |
| | | | | 606/96 |
| 2013/0023891 A1* | 1/2013 | Berberich | .......... | A61B 17/1764 |
| | | | | 606/98 |
| 2016/0089162 A1* | 3/2016 | Ardito | ............... | A61B 17/1714 |
| | | | | 606/98 |
| 2016/0302805 A1* | 10/2016 | Meridew | ............ | A61B 17/1714 |

* cited by examiner

SURGICAL DEVICE

FIELD OF THE INVENTION

This invention relates to a surgical device.

The invention finds particular application in the orthopaedic surgery field.

PRIOR ART

The following description will refer, by way of example, to a surgical device defining a drilling guide, without the invention's losing any generality thereby.

The drilling guide is a surgical device typically used in arthroscopy operations (e.g. for procedures to reconstruct a patient's knee ligaments).

To perform this kind of surgery, a tunnel (e.g. a tibial canal) needs to be created inside of which the replacement ligament is inserted and fixed inside the patient's bone.

The drilling guide enables the surgeon to insert a thin rigid wire (e.g. a "K-wire" or Kirschner wire) partially inside a bone to be operated on so that the wire can serve as a reference and guide for the subsequent creation of the tunnel.

The tunnel is in fact made by drilling the bone with a specific drilling device by arranging the drill bit around the inserted rigid wire.

The drilling guide therefore makes it possible to determine the positioning of the thin rigid wire, enabling the surgeon to drill the bone at the correct angle and at a predetermined depth of penetration.

The drilling guides of a known type are typically composed of a handling member and a guiding element. In addition, the surgical device may comprise an element for attaching the handling member to the patient's bone.

In particular, the handling member comprises a sleeve with a central slot in which the guiding element can be smoothly inserted and locking means that can be selectively activated to lock or unlock the sliding of the guiding element in the central slot.

The guiding element is, therefore, able to be moved away from and towards the bone to be operated on when the locking means are disengaged.

Typically, the surgeon can manually insert and move the guiding element in the central slot with the free hand that is not grasping the handling member. The guiding element can then be locked in suspension in the desired position by activating these locking means with the same hand that is grasping the handling member.

Once locked, the guiding element remains in the determined insertion position unless the locking means are deactivated to enable it to slide again.

However, the Applicant has observed that such locking means, typically in the form of a button or trigger, may be accidentally activated by the surgeon during surgery. A finger of the hand grasping the handling member could inadvertently slip or squeeze on the trigger, thus deactivating the locking means, effectively releasing the guiding element from the central slot and freeing its movement.

When the guiding element is free, it is therefore possible that the latter may accidentally slip out of the central slot and fall to the ground.

Due to the position and conditions of use of the surgical device, it is therefore possible that the guiding element may be unintentionally disengaged from its sliding seat and fall. In this case, the guiding element could be damaged and, in any case, become unusable as it is no longer sterile, making it necessary, therefore, to interrupt the surgical procedure. It is not possible to move the locking means activation control to a position that is not easily reached by the operator's fingers, since it is essential that the surgeon can comfortably reach the control with their fingers while grasping the device. It is, therefore, necessary to keep the control in a comfortable position but, at the same time, make it impossible to unintentionally disengage the guiding element from the central slot.

Purpose of the Invention

In this context, the technical task underlying this invention is to propose a surgical device that overcomes one or more of the above-mentioned drawbacks of the prior art.

In particular, it is the purpose of this invention to provide a surgical device that increases the safety level in using the surgical device itself, in particular to prevent the guiding element's accidentally falling during its use.

The specified technical task and purposes are substantially achieved with a surgical device comprising the technical features set forth in one or more of the accompanying claims.

In particular, this invention involves a surgical device comprising a handling member that comprises a sleeve that has a central slot and a guiding pin that radially projects inside the central slot.

The guiding element can be smoothly inserted into the central slot and comprises a tubular cylindrical body, of an elongated shape, extending along a longitudinal axis.

The guiding element has, externally, a guiding groove that is slidably coupled to the guiding pin so that the sleeve and the guiding element are mutually movable along a guiding path defined by the guiding groove.

In other words, the guiding pin is made inside the sleeve and penetrates the tubular cylindrical body at the guiding groove.

The guiding groove advantageously comprises a first and a second rectilinear groove portion angularly spaced apart about the longitudinal axis and mutually interconnected by a transversal connecting groove portion interposed between the first and second rectilinear groove portion. In other words, the two rectilinear groove portions are offset from each other in relation to the longitudinal axis.

Thanks to this invention, therefore, the guiding path is not completely rectilinear, as in the prior art devices, but has a deviation defined by a connecting groove portion that, being arranged transversely to connect the two rectilinear grooves, prevents the unintentional removal of the guiding pin from the sleeve following an unintentional movement of the guiding pin along one of the rectilinear groove portions.

The connecting groove portion basically defines an abutment wall that the pin touches (and stops) when it reaches one end of a rectilinear groove portion as a result of translatory motion along this rectilinear groove portion.

In this way, by positioning itself inside the transversal connecting groove portion, it is possible to interrupt the translation of the pin along the guiding groove to prevent unintentional translations (e.g. caused by the guiding element's falling due to gravity).

In particular, the guiding groove extends between a first end portion, defining a grip area of the guiding element, and a second end portion, opposite the first end portion, configured to be in contact with a patient's bone.

The first rectilinear groove portion extends between the first end portion and the transversal connecting groove portion and the second rectilinear groove portion extends between the transversal connecting groove portion and the second end portion.

In other words, the guiding element has a continuous, linear guiding groove defining a continuous, linear guiding path that extends from the first to the second end of the tubular body.

The guiding path is preferably basically in the form of an "S" or "Z".

The guiding element can, advantageously, be translated along a sliding direction, coinciding with the longitudinal axis, to enable the guiding pin to slide along the first and second rectilinear groove portion, while it can be rotated at least partially around the longitudinal axis thereof to enable the guiding pin to slide inside the transversal connecting groove portion.

In other words, since the transversal connecting groove portion is interposed between the two rectilinear groove portions, basically defining an intermediate section of the guiding path, the guiding element must initially be translated along the longitudinal axis thereof in order for the guiding pin to be able to run along the guiding groove from the beginning to the end, so that the guiding pin can slide along a rectilinear groove portion until abutting against the intermediate connecting groove portion, preventing any further translation along the sliding direction. The guiding element must then be rotated about the longitudinal axis thereof in order for the guiding pin to be able to move inside the transversal connecting groove portion. Finally, the guiding element must be translated, again, along the longitudinal axis thereof, so that the guiding pin can slide along the other rectilinear groove portion.

Therefore, in order for the guiding pin to be able to move along the entire guiding path, the guiding element must be intentionally rotated about its own axis. If, in fact, the pin can be unintentionally translated along the rectilinear groove portions due to gravity, the translation of the pin along the transversal connecting portion (arranged, for safety, between the two rectilinear groove portions) cannot occur unintentionally but requires the surgeon's intentional intervention, i.e. by rotating the guiding element.

In this way, the guiding pin can move from one rectilinear groove portion to the other in a controlled manner without any risk of its disengaging and falling.

In addition, the surgical device advantageously comprises locking means configured to lock the sliding of the guiding element along the sliding direction inside the central slot, and switchable between an activation configuration, wherein the movement of the guiding element inside said central slot is prevented, and a deactivation configuration, wherein the movement of the guiding element inside the central slot is free.

In this way, the surgeon can activate the locking means to lock the position of the tubular body and insert the thin rigid wire into the bone tissue once the guiding element has been positioned.

In particular, the transversal connecting groove portion is configured to prevent the sliding of the guiding element along said sliding direction during the deactivation configuration of the locking means, when the guiding pin is arranged inside the transversal connecting groove portion.

In other words, the transversal connecting groove portion defines a safety system that prevents the guiding pin from sliding between one rectilinear groove portion and the other if the locking means are unintentionally deactivated.

The locking means can preferably be selectively activated by means of a lever mechanism.

The two rectilinear groove portions are preferably angularly spaced apart by an angle at the centre ranging between 10° and 270°.

In particular, the angle at the centre must be such as to cover at least the extension of the pin; the greater the angle at the centre, the greater the length of the connecting groove portion.

According to one possible embodiment, the transversal connecting groove portion preferably extends along a surface segment of the tubular body lying on a lying plane perpendicular to the longitudinal axis of the tubular body.

In other words, the transversal connecting groove portion in this case defines a circumferential arc of the tubular body.

Therefore, in order to pass between one rectilinear groove portion and the other, the guiding pin must be translated along a circumferential arc; this operation advantageously prevents an unintentional translation of the pin from causing it to slide along the entire guiding path.

Advantageously, the surgeon must intentionally rotate the guiding element by simply rotating the guiding element about its longitudinal axis by an angle sufficient to translate the guiding pin from the transversal connecting groove portion to inside the other rectilinear groove portion.

According to an additional embodiment, the transversal connecting groove portion preferably extends along a surface segment of the tubular body lying on a plane inclined in relation to the first and the second rectilinear groove portion.

Advantageously, in this case, it is, therefore, necessary to rotate-translate the guiding element to translate the guiding pin from one rectilinear groove portion to the other along the transversal connecting groove portion.

The elbows defined along the guiding path between the rectilinear groove portions and the transversal connecting groove portion thus increase the safety level offered by the guiding element.

The first rectilinear groove portion is preferably longer than the second rectilinear groove portion.

Advantageously, this makes it possible to minimise the translation of the guiding pin along the guiding path as a result of any unintentional translation of the guiding pin.

Preferably, the first rectilinear groove portion extends beyond the transversal connecting groove portion defining a recess designed to receive the guiding pin against it to prevent circumferential sliding of said guiding pin.

Advantageously, the presence of this recess additionally increases the safety level of the guiding element.

If, in fact, the guiding pin were to unintentionally end up inside this recess, a subsequent accidental/unintentional rotation of the guiding element would not, in any case, cause the guiding pin to be translated along the transversal connecting groove portion and, thus, the guiding pin would be prevented from reaching the other rectilinear groove portion in order to run along it and accidentally slide out of the entire guiding groove.

Preferably, the second rectilinear groove portion has a lead-in chamfer at the second end portion so as to facilitate the coupling of the guiding pin with the guiding groove. Even more preferably, the lead-in chamfer leads into the second end portion.

The dependent claims, included herein for reference, correspond to different embodiments of the invention.

BRIEF DESCRIPTION OF THE DRAWINGS

Additional features and advantages of this invention will become more clear from the indicative, and therefore nonlimiting, description of a preferred, but not exclusive, embodiment of a surgical device, as illustrated in the attached drawings wherein.

DETAILED DESCRIPTION OF PREFERRED EMBODIMENTS OF THE INVENTION

With reference to the attached figures, the reference number 100 indicates a surgical device as a whole, from hereon in simply the device 100.

The device 100 comprises a guiding element 1 and a handling member 100'.

The handling member 100' comprises a sleeve 102' with a central slot 102 inside of which a guiding pin 101 extends that radially projects inside the central slot 102.

Figures 2, 2A:
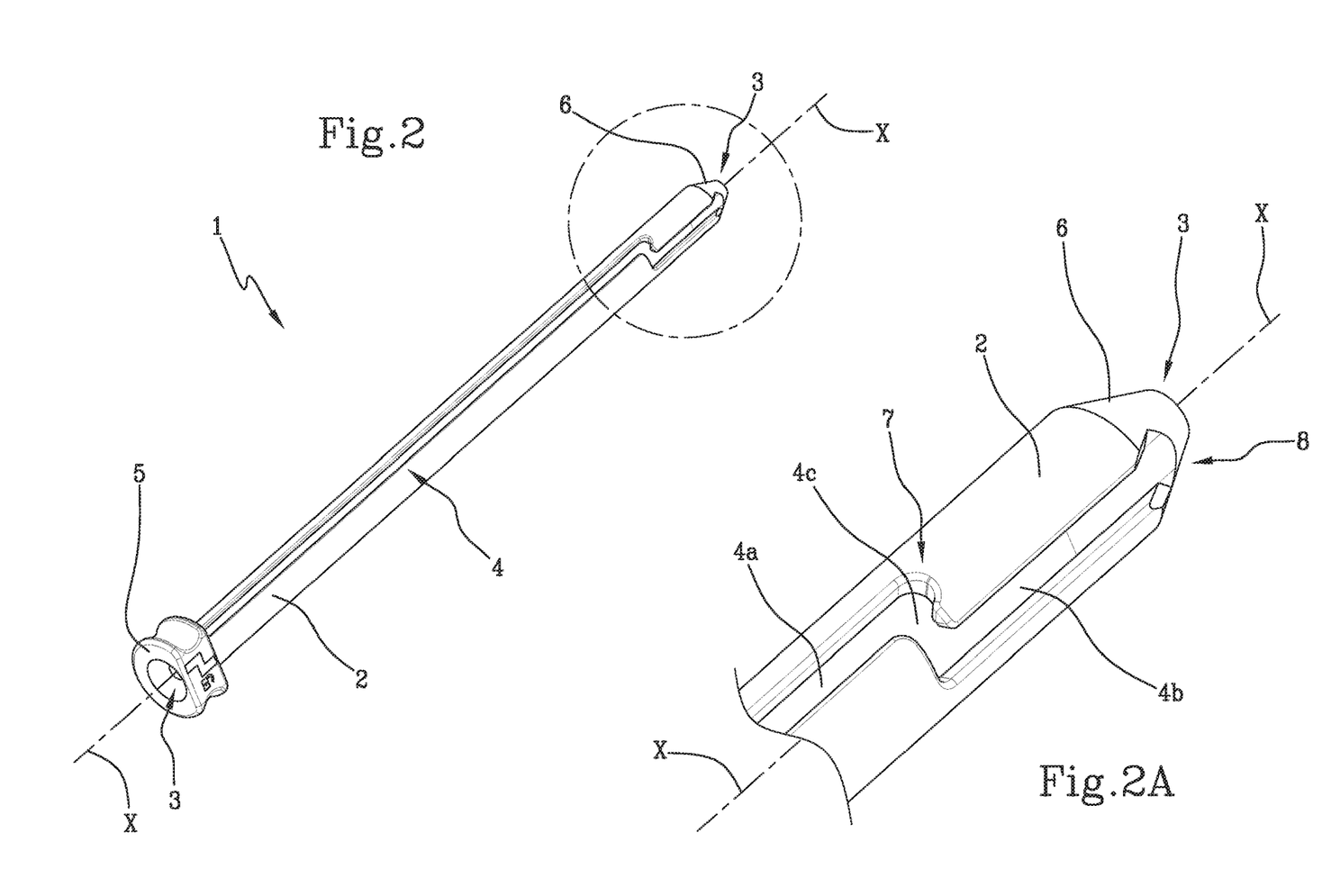
FIG. 2 is a schematic perspective view of a guiding element of the surgical device in accordance with this invention.
FIG. 2A is an enlarged view of a detail A in FIG. 2.

With reference to FIG. 2, the guiding element 1 comprises a tubular cylindrical body 2, of elongated shape, that extends along a longitudinal axis X. In particular, the tubular body 2 has a through-hole 3 configured to receive a thin rigid wire, which is not illustrated.

The tubular body 2 has, externally, a guiding groove 4 that is designed to slidably couple to the guiding pin 101 so that the guiding element 1 and the sleeve 102' of the handling member 100' are mutually movable along a guiding path defined by the guiding groove 4.

The guiding pin 101 is preferably a cylindrical prong; however, alternatively, the guiding pin 101 and the guiding groove 4 can be counter-shaped so that the guiding pin 101 can slide, but not be extracted, in the direction perpendicular to the guiding path, so the guiding pin 101 can only be inserted and extracted at the beginning and end of the guiding path.

With reference to FIG. 2A, the guiding groove 4 advantageously comprises a first 4a and a second 4b rectilinear groove portion angularly spaced apart about the longitudinal axis X and mutually interconnected by means of a transversal connecting groove portion 4c interposed between the two rectilinear groove portions 4a, 4b.

The guiding groove 4 preferably comprises only the two rectilinear groove portions 4a, 4b and the transversal connecting groove portion 4c.

The two rectilinear groove portions 4a, 4b are preferably parallel to the longitudinal axis X and angularly spaced apart by an angle at the centre ranging between 10° and 270°, preferably ranging between 20° and 180°, even more preferably equal to 60°.

In other words, the angle at the centre referred to is the angle ranging between a first plane passing through the longitudinal axis X and a first extension direction of the first rectilinear groove portion 4a and a second plane passing through the longitudinal axis X and a second extension direction of the second rectilinear groove portion 4b.

In accordance with the embodiment of the guiding element 1 illustrated in the attached figures, the transversal connecting groove portion 4c preferably extends along a surface segment of the tubular body 2 lying on a lying plane perpendicular to the longitudinal axis X of the tubular body 2. In other words, the transversal connecting groove portion 4c extends along its own extension direction defining a circumferential arc of the outer surface of the guiding element 1.

According to an alternative embodiment of the guiding element 1, which is not illustrated in the attached figures, the transversal connecting groove portion 4c extends along a surface section of the tubular body 2 lying on a plane inclined in relation to the two rectilinear groove portions 4a, 4b.

Figure 1:
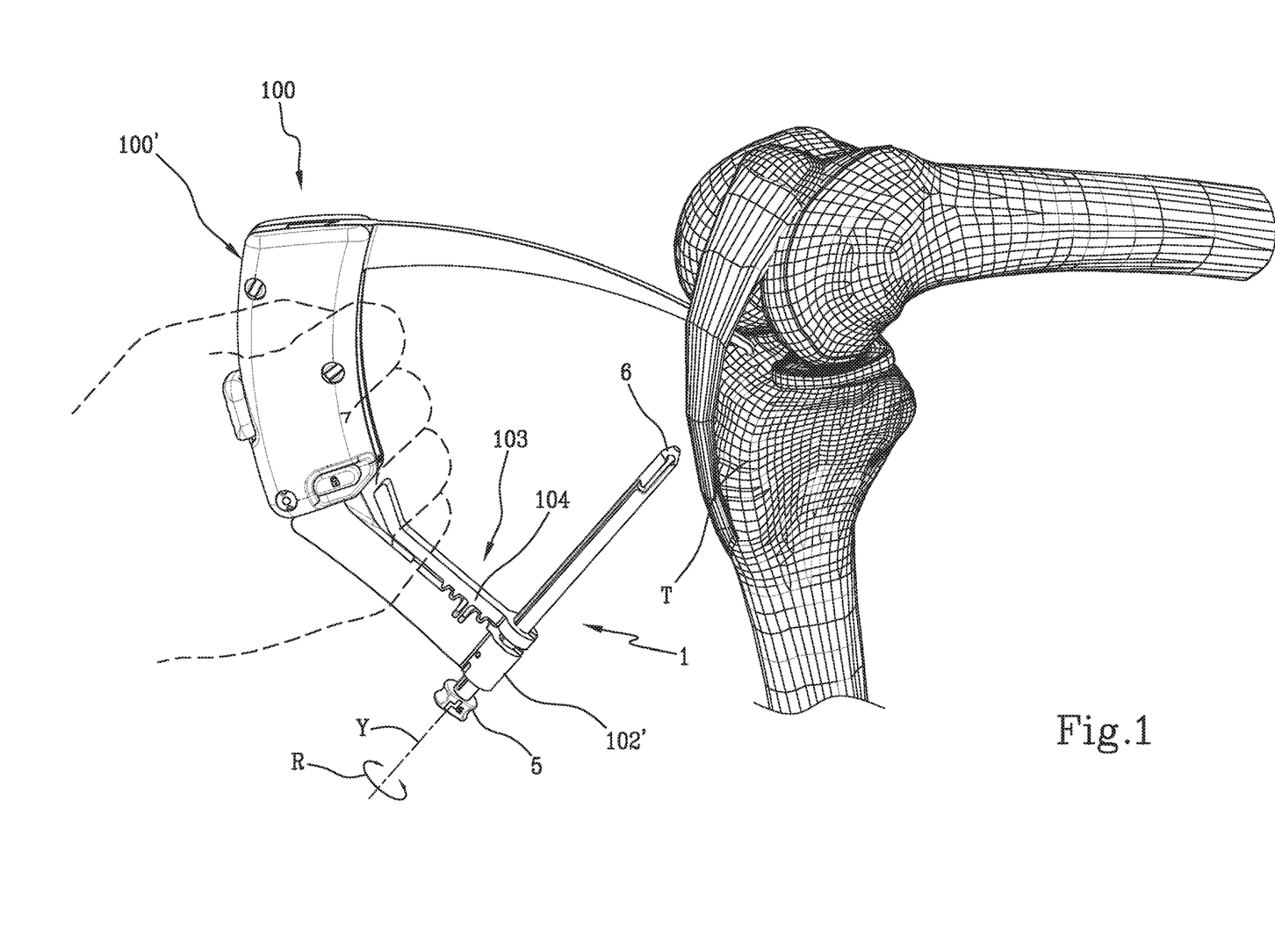
FIG. 1 is a schematic perspective view of a surgical device in accordance with this invention in use configuration.

The tubular body 2 comprises a first end portion 5, defining a grip area of the guiding element 1 through which the surgeon can act on it manually, and a second end portion 6, opposite the first end portion 5, configured to be in contact with a patient's bone (e.g. a tibia T, as illustrated in FIG. 1). In addition, the first end portion 5 defines the inlet seat for inserting the thin rigid wire.

In particular, the guiding groove 4 extends between the first end portion 5 and the second end portion 6.

The first rectilinear groove portion 4a of the two rectilinear groove portions 4a, 4b extends between the first end portion 5 and the transversal connecting groove portion 4c, and the second rectilinear groove portion 4b of the two rectilinear groove portions 4a, 4b extends between the transversal connecting groove portion 4c and the second end portion 6. Preferably, as in the embodiment in the attached figures, the first rectilinear groove portion 4a is longer than the second rectilinear groove portion 4b.

As clearly visible in FIG. 2A, preferably the first rectilinear groove portion 4a extends beyond the transversal connecting groove portion 4c defining a recess 7 suitable for receiving the guiding pin 101 against it to prevent an accidental circumferential sliding of the guiding pin 101.

The second rectilinear groove portion 4b preferably has a lead-in chamfer 8 at the second end portion 6, preferably leading into the second end portion 6.

As in the embodiment illustrated in the attached figures, the guiding groove 4 preferably comprises a single transversal connecting groove 4c interposed between the first 4a and the second 4b rectilinear groove portion. This makes it easier to mutually slide the handling member 100' and the guiding element 1.

Advantageously, the guiding pin 101 of the sleeve 102' can be smoothly inserted into the guiding groove 4 of the guiding element 1 so that the guiding element 1 is suitable for sliding inside the central slot 102 along a sliding direction Y coinciding with the longitudinal axis X of the tubular body 2.

Advantageously, the guiding element 1 can be translated along the sliding direction Y to enable the guiding pin 101 to slide along the rectilinear groove portions 4a, 4b and can be rotated at least partially about the longitudinal axis X thereof, as illustrated by the arrow R, to enable the guiding pin 101 to slide inside the transversal connecting groove portion 4c.

Advantageously, the surgical device 100 comprises locking means 103 configured to lock the sliding of the guiding element 1 along the sliding direction Y inside the central slot 102, and switchable between an activation configuration, wherein the movement of the guiding element 1 inside the central slot 102 is prevented, and a deactivation configuration, wherein the movement of the guiding element 1 inside the central slot 102 is free.

In particular, the transversal connecting groove portion 4c is configured to prevent the sliding of the guiding element 1 along said sliding direction Y during the deactivation configuration of the locking means 103, when the guiding pin 101 is arranged inside the transversal connecting groove portion 4c.

The locking means 103 can preferably be selectively activated by means of a lever mechanism 104.

Figure 3:
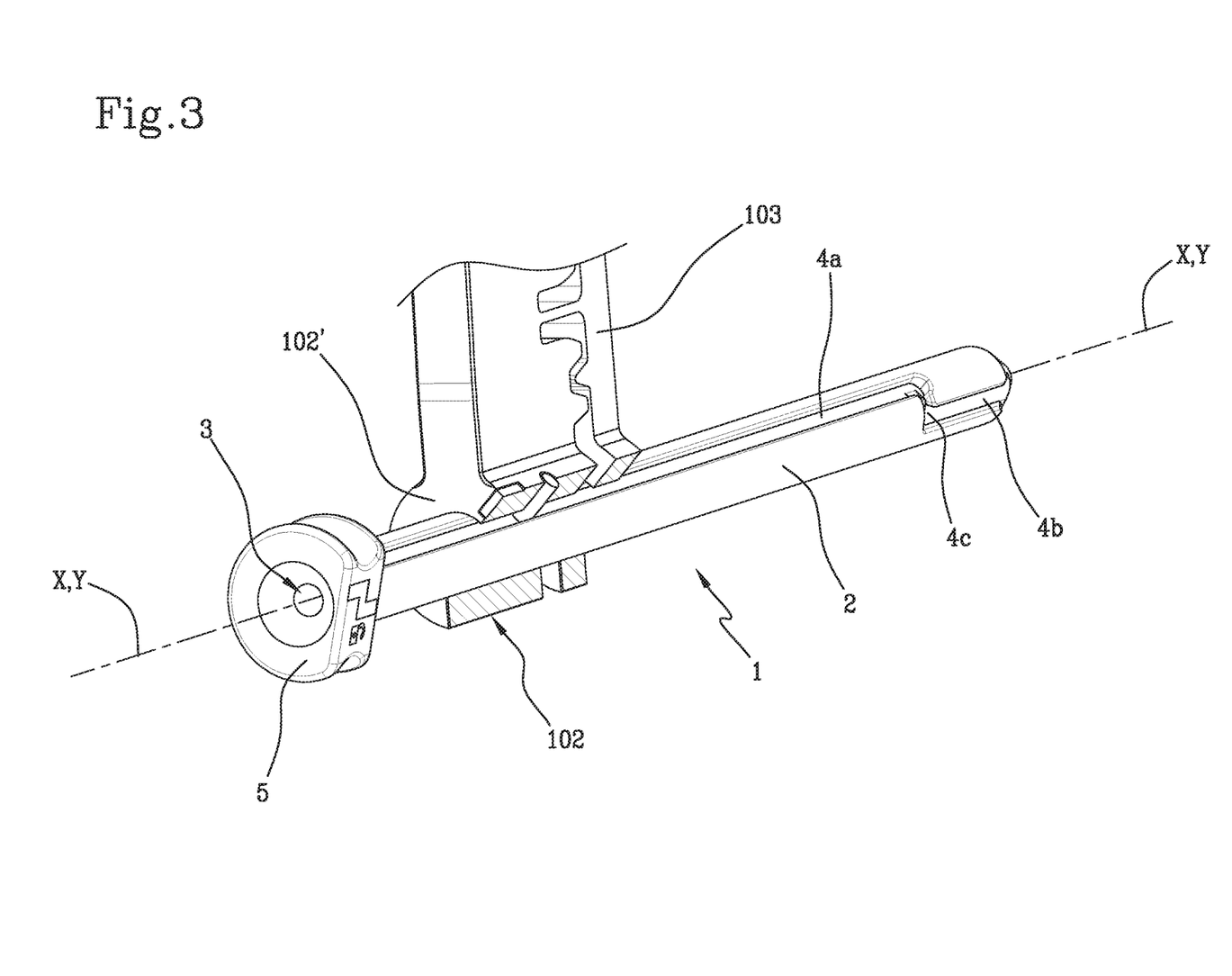
FIGS. 3, 4, and 5 are partially sectioned schematic perspective views of the guiding element in FIG. 2 in their respective operating configurations.

FIG. 3 illustrates the guiding element 1 in FIG. 1 that is slidably mobile along the sliding direction Y inside the central slot 102 during a first operating configuration in which the guiding pin 101 of the sleeve 102' is arranged inside the first rectilinear groove portion 4a.

Figure 4:
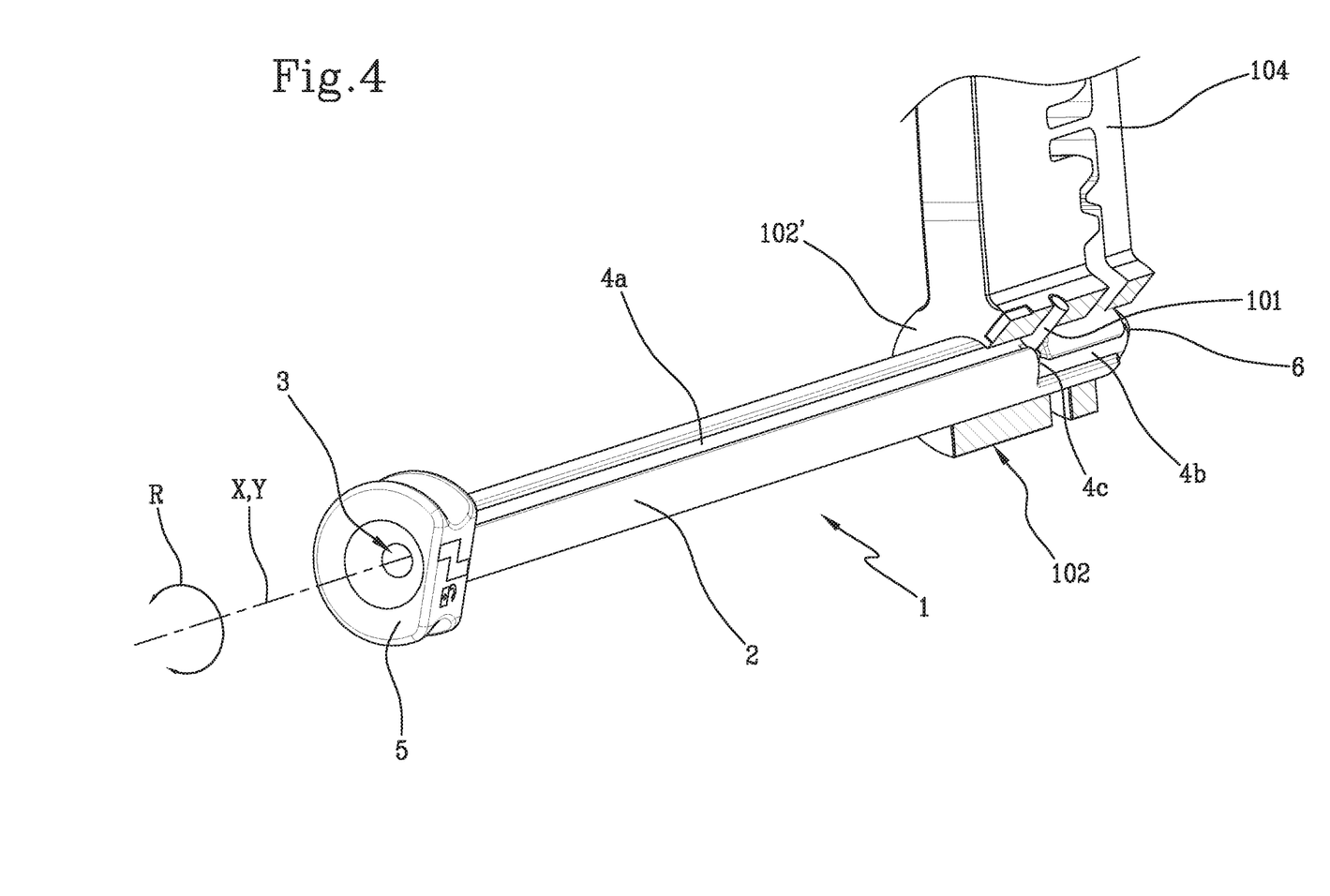
Figure 5:
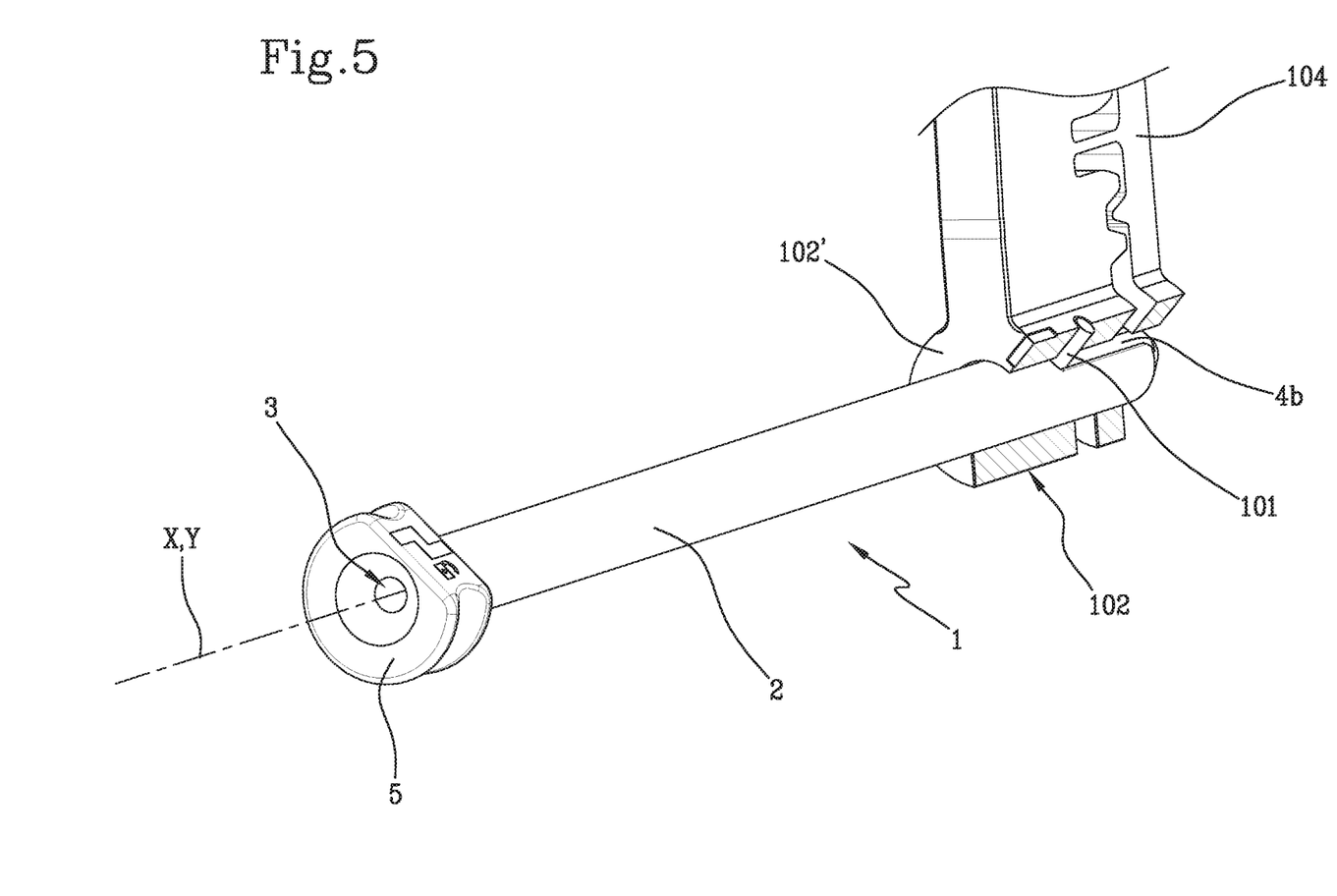

FIG. 4 illustrates the guiding element 1 in FIG. 1 in a second operating configuration in which the guiding pin 101 is arranged against the transversal connecting groove portion 4c, the stroke along the first rectilinear groove portion 4a being complete. In this position, the guiding element 1 must be rotated around the longitudinal axis X (clockwise as in the arrow R) so that guiding pin 101 can travel along the transversal connecting groove portion 4c and reach the second rectilinear groove portion 4b, reaching the third operating configuration illustrated in FIG. 5. This also applies to the reverse operation, i.e. to switch from the third configuration to the second, the guiding element 1 must be rotated (counter-clockwise as in the arrow R).

Therefore, with reference to the use position of the device 100 illustrated in FIG. 1, if the guiding pin 101 is inside the second rectilinear groove portion 4b, when the surgeon accidentally deactivates the locking means 103 by pressing their finger on the lever mechanism 104, the guiding element 1 would slip downwards, due to gravity, sliding inside the central slot 102 and the pin 101 would slide downwards inside the guiding groove 4 to the transversal connecting groove portion 4c where it would stop, effectively locking the guiding element 1 inside the central slot 102.

Therefore, the transversal connecting groove portion 4c is advantageously configured as a safety retention system for the element 1 that is able to prevent the guiding element 1 from accidentally falling.

In this case, the intentional or unintentional activation of the locking means 103 would, in any case, require the surgeon's intentional intervention to enable the guiding element 1 to be removed from the central slot 102.

This invention achieves the proposed purposes by overcoming the drawbacks complained of in the prior art and providing the user with a surgical device 100 that is equipped with a guiding element 1 that is simple to construct and enables a safety system to be produced that is able to prevent unintentional decoupling of the guiding element 1 from the handling member 100'.

The invention claimed is:

1. A surgical device comprising:
   a handling member comprising a sleeve with a central slot and a guiding pin that projects radially into said central slot, and
   a guiding element that can be slid into the central slot of said sleeve and that comprises a tubular cylindrical body of elongated shape and extending along a longitudinal axis;
   said guiding element externally having a guiding groove that is slidably coupled to a guiding pin so that said sleeve and said guiding element are mutually movable along a guiding path defined by said guiding groove;
   said guiding groove comprising a first and a second rectilinear groove portion, angularly spaced apart about said longitudinal axis, and mutually interconnected by a transversal connecting groove portion interposed between said first and second rectilinear groove portions; wherein the guiding groove extends between a first end portion, defining a grip area of the guiding element, and a second end portion, opposite to the first end portion, configured to be arranged in contact with a bone of a patient;
   said first rectilinear groove portion extending between the first end portion and the transversal connecting groove portion, and said second rectilinear groove portion extending between the transversal connecting groove portion and the second end portion;
   said guiding element being translatable along a sliding direction, coinciding with the longitudinal axis, to allow sliding of the guiding pin along the first and the second rectilinear groove portion,
   wherein upon receipt of the guiding pin within said guiding groove, said guiding element is at least partially rotatable about the longitudinal axis of the guiding element when the guiding pin slides along the transversal connecting groove portion of the guiding groove;
   wherein said surgical device comprises locking means configured to lock the sliding of the guiding element along the sliding direction inside the central slot, and switchable between an activation configuration, wherein movement of the guiding element inside said central slot is prevented, and a deactivation configuration, wherein movement of the guiding element inside said central slot is free; and
   said transversal connecting groove portion being configured to prevent sliding of the guiding element along said sliding direction during the deactivation configuration of the locking means, when the guiding pin is arranged within said transversal connecting groove portion.

2. The surgical device according to claim 1, wherein said locking means can be selectively activated by a lever mechanism.

3. The surgical device according to claim 1, wherein a central axis of each of said first and said second rectilinear groove portions is parallel to the longitudinal axis and angularly spaced apart from each other by an angle ranging between 10° and 270°.

4. The surgical device according to claim 1, wherein the transversal connecting groove portion extends along a surface segment of the tubular cylindrical body lying on a lying plane perpendicular to the longitudinal axis of the tubular cylindrical body.

5. The surgical device according to claim 1, wherein the transversal connecting groove portion extends along a surface segment of the tubular cylindrical body lying on a plane which is inclined with respect to said first and said second rectilinear groove portions.

6. The surgical device according to claim 1, wherein said first rectilinear groove portion is longer than the second rectilinear groove portion.

7. The surgical device according to claim 1, wherein said first rectilinear groove portion extends beyond the transversal connecting groove portion defining a recess designed to receive the guiding pin against it to prevent circumferential sliding of said guiding pin.

8. The surgical device according to claim 1, wherein the second rectilinear groove portion has, at the second end portion, a lead-in chamfer, preferably leading into said second end portion, in order to facilitate coupling of the guiding pin with the guiding groove.

9. The surgical device according to claim 1, wherein the guiding groove comprises a single transversal connecting groove portion interposed between the first and the second rectilinear groove portion.

* * * * *